United States Patent [19]

Elliott et al.

[11] Patent Number: 4,853,946
[45] Date of Patent: Aug. 1, 1989

[54] DIAGONOSTIC SERVICE SYSTEM FOR CT SCANNERS

[75] Inventors: Richard J. Elliott, Akron; Walter A. Dupuis; Theodore A. Resnick, both of Cleveland Hts., all of Ohio

[73] Assignee: Picker International, Inc., Highland Hts., Ohio

[21] Appl. No.: 201,405

[22] Filed: Jun. 2, 1988

Related U.S. Application Data

[63] Continuation of Ser. No. 931,548, Nov. 14, 1986, abandoned.

[51] Int. Cl.$^4$ ............................................... H05G 1/60
[52] U.S. Cl. .......................................... 378/4; 378/98; 378/207
[58] Field of Search ................... 378/4, 114, 117, 118, 378/98, 207; 371/16, 20, 29; 364/414, 550, 551

[56] References Cited

U.S. PATENT DOCUMENTS

| | | | |
|---|---|---|---|
| 3,805,038 | 4/1974 | Buedel et al. | 235/153 |
| 3,955,119 | 5/1976 | Perry et al. | 315/133 |
| 4,032,789 | 6/1977 | Workman | 250/445 |
| 4,477,901 | 10/1984 | Braband et al. | 371/15 |
| 4,497,057 | 1/1985 | Kato et al. | 371/29 |
| 4,499,581 | 2/1985 | Miazga et al. | 371/20 |
| 4,517,468 | 5/1985 | Kemper et al. | 290/52 |
| 4,520,495 | 5/1985 | Tanaka | 378/17 |
| 4,578,767 | 3/1986 | Shapiro | 364/550 |
| 4,586,147 | 4/1986 | Tadokoro | 364/550 |

OTHER PUBLICATIONS

Logic Data Book of National Semiconductor Corp., vol. 1, pp. 6–110 and 6–114, 1984.
"Practical Digital Design Using IC's" by Joseph D. Greenfield, published by John Wiley & Sons, Inc. 1977, pp. 159, 160, and 166.

*Primary Examiner*—Craig E. Church
*Attorney, Agent, or Firm*—Fay, Sharpe, Beall, Fagan, Minnich & McKee

[57] ABSTRACT

A plurality of medical electronic apparatae (A) including a CT scanner (B) or other medical imaging equipment are disposed at each of a plurality of remote locations. A diagnostic service system (C) monitors each CT scanner to create a malfunction history therefor. A central polling station (D) polls the diagnostic service system of each scanner to retrieve the diagnostic history thereof. The diagnostic service system includes a plurality of monitors (80, 82, 84, 86, 88) which monitor operating conditions and parameters of the scanner. The monitored operating conditions include the operating mode within the sequence of operating modes, operating parameters of an X-ray tube (12), and the operation of other scanner components. When a fault detection circuit (92) detects a malfunction, a latch array (90) immediately stores an indication of the condition monitored by the monitors. A read/write circuit (94) transfers the latched condition data to a malfunction history memory (96). Data from the malfunction history memory may be displayed on diagnostic service display (104) or transmitted by a modem (112) to the central polling station.

21 Claims, 1 Drawing Sheet

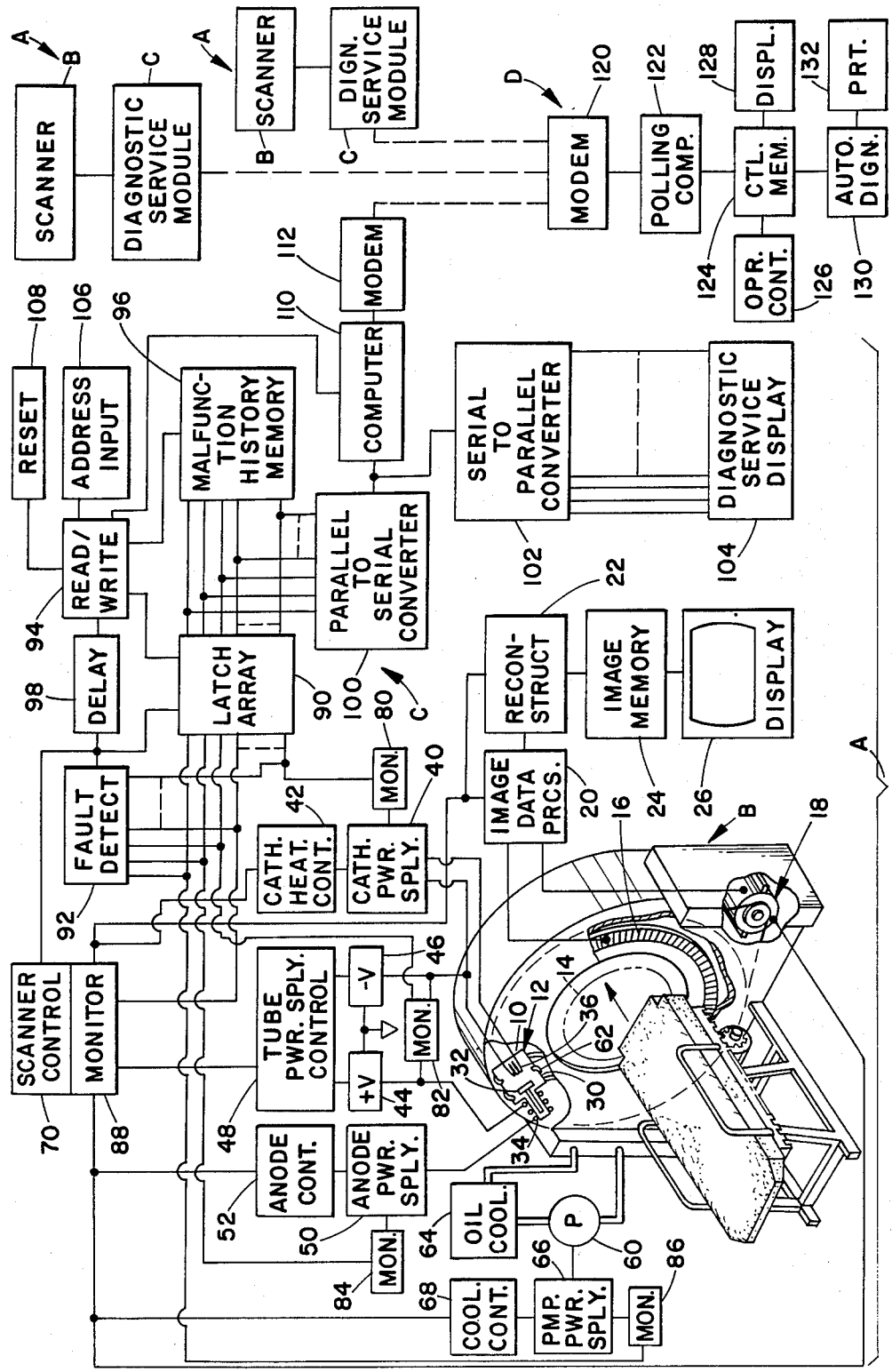

DIAGONOSTIC SERVICE SYSTEM FOR CT SCANNERS

This is a continuation of application Ser. No. 931,548, filed Nov. 14, 1986, now abandoned.

BACKGROUND OF THE INVENTION

The present invention relates to the field of electronic malfunction monitoring and diagnosis. It finds particular application in conjunction with computerized tomographic scanners and will be described with particular reference thereto. However, it is to be appreciated that the invention may also find application in conjunction with other imaging apparatus, other medical electronic equipment, and the like.

Heretofore, various malfunction indicators have been provided for CT scanners. Most commonly, an LED was interconnected with each of various electronic components of the scanner. Each LED was illuminated or dark in accordance with the state of the associated electronics. However, a malfunction in a CT scanner often triggered subsequent malfunctions. The illuminated diodes only reflected the state of the monitored electronics at the end of the series of malfunctions. No indication was provided of the malfunction which triggered the sequence of malfunction events.

To improve diagnostic capability, a plug-in diagnostic system has also been provided. Rather than or in addition to the LEDs, the service technician was provided with a plug-in diagnostic module. The plug-in module monitored the state of a plurality of monitored electronic circuits and provided an indication of the state thereof. A plug-in module carried by the service technician, however, was only effective when monitoring for impending maintenance problems and for analyzing a system malfunction after the fact. Again, when a malfunction sequence occurred, no indication of the initial, triggering malfunction was provided.

In accordance with the present invention, a new and improved distributed diagnostic system is provided for CT scanners which overcomes the above identified drawbacks and provides more meaningful service information.

SUMMARY OF THE INVENTION

In accordance with one aspect of the present invention, a diagnostic service system is provided for medical diagnostic scanners. A monitor means monitors each of a plurality of scanner operating conditions. A latch array operatively connected with the monitor means is provided for selectively storing an indication of each monitored condition in one latch of the array. Upon detection of a malfunction, a fault detection means causes the latches to hold each monitored condition. In this manner, the latches hold the monitored conditions, whether the monitored conditions are in or out of a normal operating range, to provide a snap shot of the state of all monitored conditions at the initial detection of the malfunction. A malfunction history memory means is provided for storing the monitored conditions from the latches after each of a plurality of detected malfunctions to create a malfunction history.

In accordance with a more limited aspect of the present invention, the medical diagnostic scanner is a CT scanner. The monitor means monitors at least one of (i) an X-ray tube anode operating condition, (ii) a cathode operating condition, (iii) an X-ray tube operating voltage, and (iv) in which of a sequence of operating modes the scanner was operating when the malfunction occurred.

In accordance with another aspect of the present invention, a diagnostic service system is provided. Each of a plurality of medical diagnostic apparatae are provided with a plurality of monitors that monitor operating conditions or parameters of selected components. The plurality of monitors are operatively connected with a latch array which includes at least one latch for temporarily storing or holding a corresponding monitored condition. A fault detection means detects malfunctions and causes the latch array to hold an indication of each monitored condition in response to detection of the malfunction. A malfunction history memory stores a plurality of the monitored conditions from the latches after each of a plurality of detected malfunctions to create a malfunction history. A central polling computer regularly accesses the malfunction history memory means of each of the plurality of medical diagnostic apparatae and retrieves the stored malfunction history therefrom. In this manner, the central polling computer maintains a malfunction history for each of the plurality of medical apparatae at a central location to facilitate apparatus maintenance scheduling, malfunction diagnoses, and repair.

In accordance with another aspect of the present invention, the method is provided for diagnosing CT or other medical scanner malfunctions. A plurality of scanner operating conditions are monitored. Immediately upon detecting a malfunction, indications of each of the monitored conditions are stored to provide a snap shot of the monitored conditions when the malfunction occurred. Preferably, each malfunction condition of a plurality of snap shots are stored to maintain a retrievable malfunction history for the scanner.

In accordance with a more limited aspect of the present invention, the malfunction history of each of a plurality of scanners or other medical electronic apparatae are periodically polled from a central location such that the malfunction histories of the plurality of medical electronic apparatae are maintained at the central location. In this manner, service and maintenance calls can be coordinated with the needs of each individual medical electronic apparatus.

One advantage of the present invention is that it facilitates efficient repair.

Another advantage of the present invention is that it expedites effective preventive maintenance on an as-needed basis.

Another advantage of the present invention is that it minimizes scanner down time.

Still further advantages of the present invention will become apparent to those of ordinary skill in the art upon reading and understanding the following detailed description of the preferred embodiment.

BRIEF DESCRIPTION OF THE FIGURE

The invention may take form in various components and arrangements of components or in various steps and arrangements of steps. The figure is only for purposes of illustrating a preferred embodiment and is not to be construed as limiting the invention.

The FIGURE is a diagrammatic illustration of CT scanner and diagnostic service system in accordance with the present invention.

DETAILED DESCRIPTION OF THE PREFERRED EMBODIMENT

With reference to the FIGURE, a medical electronic apparatus A includes a CT scanner B, another type of medical imager, or the like. The apparatus also includes a diagnostic service module C which monitors the operating conditions and parameters of the scanner B to provide a record thereof. A central monitoring station D is interconnected with a plurality of the diagnostic service modules for periodically accessing and retrieving a record of the monitored scanner operating conditions and parameters.

The scanner B includes a gantry 10 on which an X-ray tube 12 is mounted. The X-ray tube selectively projects a fan of radiation across a scan circle 14 to impinge upon an X-ray detector array 16. A gantry rotating means 18 selectively rotates the X-ray tube around the scan circle such that the detector array 16 receives radiation which has traversed the scan circle from a plurality of directions. An image data processing means 20 is interconnected with the detector array 16 to receive electronic signals indicative of the intensity of radiation received by each detector periodically during each scan and the relative position of the X-ray tube. The image data processor reorganizes, filters, and processes the image data from the detector array into an appropriate format for reconstruction by an image reconstructing means 22. The image reconstruction means 22 reconstructs the image data into an image representation which is stored in an image memory 24 and selectively displayed on a video monitor or other display means 26.

The X-ray tube 12 includes an evacuated envelope 30 in which an anode 32 is rotatably mounted. Anode motor windings 34 are disposed around the evacuated envelope adjacent the anode for selectively providing a rotational torque thereto. At least one of a directly or indirectly heated cathode 36 is disposed within the evacuated envelope adjacent the anode for selectively supplying an electron beam to excite the stimulation of X-rays on the anode. Preferably, a second, low energy cathode is also provided.

A cathode power supply 40 under the control of a cathode heating control means 42 selectively provides a heating current for heating the cathode. The heating current is controlled such that an appropriate preselected cathode temperature is maintained to boil off an adequate supply of electrons. In the preferred embodiment, the cathode control means 42 controls the flow of current through a cathode heating filament. The filament may function as the cathode itself or may heat a separate cathode.

A split voltage tube-power supply includes a positive power supply portion 44 and a negative power supply portion 46. The positive power supply portion 44 maintains the anode at a preselected positive voltage relative to ground, commonly in the 50 to 70 kilovolt range. The negative voltage supply 46 maintains the cathode at a preselected negative voltage, normally in the $-50$ to $-70$ kilovolt range relative to the common ground. A tube power supply control means 48 controls the positive and negative power supplies for selectively causing an appropriate potential difference across the anode and the cathode to cause an electron flow therebetween of a selected energy to excite x-radiation of a selected wave length.

In order to inhibit degradation of the anode, an anode rotating means is provided such that the anode surface moves continuously relative to the electron beam. An anode power supply 50 selectively provides motive power to the anode windings 34 to cause the anode 32 to rotate. An anode rotation control means 52 controls the rotation of the anode.

An X-ray tube cooling means selectively circulates a cooling fluid, such as oil, adjacent the X-ray tube, particularly the anode, to inhibit overheating. In the preferred embodiment, the cooling means includes a pump 60 for pumping the cooling fluid adjacent an X-ray tube envelope within a tube housing 62. An oil cooler, such as an oil/air radiator 64 cools the oil before it is recirculated by the pump 60. A pump power supply 66 under the control of a coolant control means 68 selectively enables the pump 60 to circulate the coolant fluid.

A scanner control means 70, such as a microprocessor, selectively controls the X-ray tube rotating means 18, the cathode control means 42, the tube power control means 48, the anode rotator control means 52, the coolant control means 68, the image data processor 20, the image reconstruction means 22, and other operating parts of the scanner B. In a preferred mode of operation, the scanner control means causes the scanner sequentially to assume preselected states or operating modes.

In a stand-by mode or state, power is supplied to the various control circuits such that they are ready to respond to a command. However, substantially all of the operating systems of the scanner are in a quiescent state. When an exposure is to be taken, the anode rotor control means 52 causes the anode to start rotating to bring it up to the preselected speed. In a preheat mode, the filament is warmed from a warm stand-by temperature to a preselected exposure temperature. In an exposure mode, the tube power supply control means 48 places a preselected operating potential across cathode and anode to cause a generation of a fan beam of X-rays. The X-ray tube rotating means 18 causes the X-ray tube to rotate as the image data processor 20 is enabled to process the collected image data and the reconstruction means 22 is enabled to reconstruct the data into the image representation. In a phase down mode, the tube power control means 48 terminates the supply of voltage across the cathode and the anode. The cathode heating means 42 causes the filament current to be reduced at a preselected rate to reduce the cathode temperature in a controlled manner. The coolant control means 68 continues to circulate the cooling fluid. After the phase down mode if another exposure is to be taken immediately, the scanner control means 70 returns to the preheat mode and repeats the sequence operating modes. After phase down if another exposure is not imminent, then the scanner optionally enters an anode brake mode followed by the stand-by mode.

The diagnostic service module C includes a plurality of monitors for monitoring each of a plurality of operating conditions or parameters of the scanner B, such as the operating mode and the functioning of various scanner components. In the preferred embodiment, the plurality of monitors includes a cathode monitor 80 for monitoring a condition indicative of cathode heating such as the heating current provided to the filament. In the preferred embodiment, the cathode monitor is connected with the filament current supply 40 to monitor whether it is operating properly. The cathode monitor 80 is a binary monitor, in the preferred embodiment, which produces a "1" output when the preselected current is being applied to the filament and a "0" output signal when an improper filament current is passing through the filament. Optionally, additional monitors may be provided for monitoring other conditions concerning the cathode filament current, the cathode control means, or the filament power supply.

A tube power monitor 82 is interconnected between the positive and negative power supplies to determine whether they are in balance. That is, in the preferred embodiment, the positive and negative power supplies produce voltages which are the same number of volts off from the common potential, one in the positive direction and the other in the negative. If the absolute voltage deviation of the two power supplies from the common ground does not match, a tube power error signal is provided. Again, the tube power monitor 82 is a binary monitor which produces a "1" when the selected tube voltage is supplied and a "0" when an improper tube voltage is supplied. Optionally, other monitors may be provided for monitoring other aspects of the electrical potential applied across the anode and cathode filament, other operating parameters of the positive or negative power supply, or the operating parameters of the tube power supply control means.

An anode rotation monitor 84 monitors a condition which is indicative of whether or not the anode is rotating at the selected speed. In the preferred embodiment, the anode rotation monitor is connected with the anode rotator power supply to determine whether the appropriate power is being supplied to the coils 34. Optionally, other monitoring means may be provided for monitoring the actual rotation of the anode, the power flowing through the windings 34, other operating parameters of the anode rotation power supply 50, or operating parameters of the anode rotation control means 52.

A coolant monitor 86 monitors whether the cooling system 60 is functioning properly. In the preferred embodiment, the coolant monitor 86 monitors whether the pump power supply 66 is providing the appropriate electrical power to the pump 62. Optionally, the same monitor or additional monitors may be provided measuring the temperature of the cooling fluid, monitoring the actual pumping rate of the pump 62, operating parameters of the coolant control means 68, or operating parameters of the pump power supply means 66.

A mode monitor 88, such as a sequence monitoring board, monitors which of the above described operating modes the scanner is presently in. The mode monitor determines which mode the scanner control means 70 has ordered at a point in the operating sequence that a fault occurs. Optionally, the mode monitor may monitor the control signals actually sent by the scanner control to each of the scanner components for consistency with the ordered mode. Any inconsistency is indicative of malfunctioning in the control means 70.

Preferably, a large multiplicity of operating conditions in addition to those described above are also monitored. It is to be appreciated that the operating conditions may be monitored directly or indirectly. In many instances it is more expeditious to monitor a related operating condition or parameter which is indicative of a selected operating condition. For example, the supply of proper power levels to the anode rotor is indicative, although not conclusively, of whether the anode is rotating. Such indirect monitoring is herein considered to be monitoring the selected operating conditions.

A latch array 90 includes a plurality of latches, each of which is connected with one of the above discussed monitors and other monitors throughout the scanner. When enabled, each latch latches or holds the current state of the corresponding monitor including the operating parameters of system components and the point in the operating sequence at which the fault occured. In this manner, the sate of output of all of the monitors is stored each time the latch array is enabled to take a "snap shot" of the monitored operating parameters and conditions of the scanner as well as the malfunction.

A fault detection means 92 detects system malfunctions. The fault detection means is connected with each of the monitors to detect when any of the monitors monitor an erroneous or inappropriate parameter or condition. In one embodiment in which a "1" from the monitor indicates a proper monitored condition and a "0" indicates an improper one, the fault detection means looks for a change from a "1" output to a "0" output from any one of the monitors. The fault detection means may advantageously be incorporated in the sequence monitoring logic with the mode monitor 88.

Various system malfunctions may be responsible for the detected malfunction. For example, the scanner control means 70 might send out control signals with inappropriate timing. One of the timing signals may be too long, too short, fail to turn on, fail to turn off, or the like. Another common cause of malfunctions is a weak or aging X-ray tube. As an X-ray tube weakens, the tendency for it to arc increases. When the X-ray tube arcs, the potential between the cathode and the anode is altered and a malfunction condition monitored. Normally, no permanent damage is done. When the machine is again energized, it will perform normally without repair. As the X-ray tube continues to age, arcing of the tube can be expected to become more common. Because the X-ray tubes of CT scanners often run on the order of $30,000.00, some hospitals choose to tolerate a fair rate of arcing malfunctions before replacing the tube.

In response to detecting an error or malfunction, the fault detector 92 produces a trigger signal on an output line thereof. The output line is connected with the latch array 90 to cause the latches to latch or store the present state of each monitor. Optionally, a short delay, such as a 10 microsecond delay, may be provided such that the latches are not triggered by spurious noise. Preferably, any delay should be sufficiently short that the latches record the operating parameters and conditions at the initial malfunction. The fault detection means output line is also connected with the scanner control means 70 to cause the scanner control means to switch the operating components of the scanner from their present state to the phase down mode. The trigger signal also enables a read/write means 94 which causes the latched information in the latch array 90 to be transferred to a malfunction history memory means 96. Optionally, a delay means 98 may be provided such that the data from the latches is not transferred to the malfunction history memory until the latches have set. Upon completion of the transfer of the latched data, the latches are reset. Preferably, the latches are reset by a signal which indicates that the detected malfunction is no longer present. Optionally, several sets of data may be transferred through the latch array to the malfunction history memory during a domino effect sequence of cascading malfunctions.

Although the latches of the latch array 90 are shown as being in a common location remote from the monitors, it is to be appreciated that each latch may be physically located adjacent or incorporated in the corresponding monitor. The read/write means 94 may include a microprocessor which is enabled in response to a detected malfunction to poll each of the remote latches and transfer the polled data to the malfunction history memory means 96.

The read/write means 94 also causes the malfunction history memory 96 to read out at least the most recently recorded set of malfunction parameters and conditions to a parallel to serial converter 100. A serial to parallel converter 102 converts the serial formated data into parallel formated data to enable each indicator of an LED or other indicator array or display means 104 to be actuated or not actuated in accordance with the state of the corresponding monitor when the fault was detected. Other display means 104 which provide an indication of each monitored system parameter and operating condition at the initial stage of the most recently detected malfunction are also contemplated. An address input means 106 is operated by a repair technician to cause the read/write means 94 to address selected prior malfunction data sets for display on the display means 104. In this manner, the repairman can monitor the history of the scanner. Upon completion of the repair, the service technician can operate a reset means 108 to erase the malfunction history memory such that all its storage capacity is available to store upcoming malfunctions.

A computer 110 selectively transfers the serial data from the parallel to serial data converter means 100 to a modem 112, such as a telephone modem, and receives data retrieval commands from the modem. More specifically, the central polling means D calls upon the modem 112 at regular intervals or upon demand to cause the computer 110 to command the read/write control means 94 to transfer selected data from the malfunction history memory 96 to the parallel to serial converter for transmission by the modem to the central polling station D. As requested by the central polling station, the computer 110 causes the read/write control means 94 to read the most recent malfunction data set and one or more preceding malfunction data sets from the malfunction history memory.

The central polling station D includes a modem 120 which is controlled by a polling computer 122 to address the diagnosis service module modem 112 of each of a plurality of the medical electronic apparatae. The polling computer 122 sends the appropriate commands through the modems to the read/write control means 94 of the addressed diagnostic service module to retrieve the malfunction data sets from the malfunction history memory as may be necessary to bring a corresponding malfunction history for that scanner in a central memory means 124 up to date. An operator control means 126 enables an operator to retrieve selected information from the central memory 124 for display on a central polling station display 128. In this manner, a service technician can monitor the malfunction history of each of the medical electronic apparatus for which he is responsible from a central location.

Optionally, an automatic diagnosis means 130 may compare each retrieved malfunction data set with a plurality of preselected malfunction data sets, each of the preselected data sets being indicative of one or more types of malfunctions, preferably those malfunctions which require prompt servicing attention. A display means, such as a printer 132, is connected with the automatic diagnosis means 130 to print a service order indicative of the medical electronic apparatus which requires attention and the nature of the repair required.

The invention has been described with reference to the preferred embodiment, obviously modifications and alterations will occur to those skilled in the art upon reading and understanding the preceding specification. It is intended that the invention be construed as including all such alterations and modifications insofar as they come within the scope of the appended claims or the equivalents thereof.

Having thus described the preferred embodiment, the invention is now claimed to be:

1. A CT scanner comprising:
   an x-ray tube mounted to rotate an x-ray beam around a scan circle, the x-ray tube including an evacuated envelope, a rotatable anode disposed in the envelope, means for rotating the anode, and at least one cathode disposed in the envelope;
   an anode rotating means power supply for supplying motive power to the anode rotating means;
   a cathode power supply for heating the cathode;
   a tube power supply for providing an electrical potential between the anode and the cathode;
   a cooling fluid means for circulating a cooling fluid adjacent the evacuated envelope to limit the heating of the x-ray tube;
   an x-ray detector array disposed across the scan circle from the x-ray tube to receive x-rays which have traversed a region of interest of a patient;
   an x-ray beam rotating means for rotating the x-ray beam around the scan circle;
   an image reconstruction means for reconstructing image representations, the image reconstruction means including means for receiving information from the detector array regarding the intensities of the x-rays which have traversed the region of interest and reconstructing an image of a cross section of the patient;
   a scanner control for controlling the anode power supply, the cathode power supply, the tube-power supply, the cooling fluid means, the anode rotating means, the image reconstruction means and a sequence operating mode thereof;
   an anode monitor for monitoring whether motive power is being supplied to the anode rotating means;
   a cathode monitor for monitoring the cathode power supply;
   a tube power monitor for monitoring the electrical potential between the anode and the cathode;
   a cooling fluid monitor for monitoring the cooling fluid;
   a scanner sequence control monitor for monitoring the controlled operating mode;
   a latch array including at least one latch operatively connected with each monitor for selectively latching in temporary storage corresponding monitored conditions to create a "snap shot" of the monitored operating conditions;
   a fault detection means for detecting malfunctions, the fault detection means being operatively connected with the monitors for determining malfunctions from the monitored conditions and being operatively connected with the latch array for causing each latch to latch into storage the corresponding monitored condition as monitored by the monitor to which it is connected before the detected malfunction cascades causing further changes of the monitored conditions, such that the snap shot of the state of the monitored conditions is taken when a malfunction is detected to aid diagnosis and repair; and, a malfunction history memory means for storing long term the monitored conditions latched by the latches in response to each of a plurality of detected malfunctions to create a malfunction history for the CT scanner including a plurality of snap shots of the monitored conditions recorded at the time of each malfunction, such that the malfunction history aids diagnosis and repair.

2. The CT scanner as set forth in claim 1 further including:

a central polling computer means for polling the malfunction history memory means of a plurality of CT scanners to retrieve the stored malfunction history therefrom and transfer the retrieved malfunction histories into a central location to facilitate diagnosis of malfunctions from the central location.

3. The CT scanner as set forth in claim 1 wherein the tube power supply includes a positive power supply for supplying the anode with a preselected positive voltage relative to a common ground and a negative voltage supply for supplying a preselected negative voltage to the cathode relative to the common ground, and wherein the tube power monitor monitors a balance between the positive and negative potentials supplied by the positive and negative power supply means for an imbalance therebetween.

4. A diagnostic service system for CT scanners, the system comprising:

an anode monitor for monitoring an x-ray tube anode;

a cathode monitor for monitoring an x-ray tube cathode;

a tube power monitor for monitoring a selected electrical potential applied between the anode and the cathode;

a latch array including a plurality of latches, at least one latch being operatively connected with each of the anode, cathode, and tube power monitors for continuously receiving a corresponding monitored condition until a latch clock signal is received, each latch being responsive to a latch clock signal to store the corresponding monitored condition in memory before a malfunction cascades and affects other monitored conditions;

a fault detection and latching means for detecting malfunctions, the fault detection means being operatively connected with the anode, cathode, and tube power monitors for determining malfunctions from the monitored conditions, the fault detection means being operatively connected with the latch array for providing the latch clock signal to each latch to latch the monitored condition of the corresponding monitor in memory;

a malfunction history memory means for storing the monitored conditions, the memory means being operatively connected with the latch array such that monitored conditions stored in the latch are selectively transferred to the memory means for each of a plurality of detected malfunctions to create a malfunction history; and, a display means for displaying selected portions of the malfunction history.

5. The system as set forth in claim 4 further including a sequence monitor for monitoring operating modes of the scanner, the latch array including a latch which is operatively connected with the sequence monitor for selectively latching an indication of the monitored operating mode when the malfunction was detected.

6. The system as set forth in claim 4 further including:

a central polling computer means for polling the malfunction history memory means of each of a plurality of diagnostic service systems to retrieve the malfunction histories therefrom.

7. The system as set forth in claim 6 further including modems interconnected with the central polling computer means and with the malfunction history memory means such that data is transmitted therebetween.

8. The system as set forth in claim 6 further including an automatic diagnosis means for comparing retrieved malfunction histories with preselected malfunction histories which are indicative of one or more malfunctions.

9. A medical diagnostic scanner system comprising:

a source of penetrating radiation;

a detector means for detecting radiation that has traversed an examination region and generating electronic detector data indicative thereof;

an image reconstruction means for reconstructing an image representation from the electronic detector data;

a monitor means for monitoring each of a plurality of scanner operating conditions;

a latch array including a plurality of latches operatively connected with the monitor means, each latch being responsive to a clock signal to freeze the corresponding one of the monitored conditions in temporary storage;

a fault detection means for detecting malfunctions, the fault detection means being operatively connected with the monitor means for determining malfunctions from the monitored conditions, the fault detection means being operatively connected with the latch array for clocking each latch to latch and freeze the corresponding monitored condition in response to a determined malfunction such that the latch array captures a snap shot of each monitored condition before a detected malfunction can cascade and affect other monitored conditions;

a malfunction history means for storing the monitored conditions, the malfunction history means being operatively connected with the latch array such that monitored conditions latched in temporary storage in the latch are selectively transferred to the malfunction history means for each of a plurality of detected malfunctions to create a malfunction history; and, a display means for displaying selected portions of the malfunction history.

10. The system as set forth in claim 9 wherein the monitor means includes a monitor for monitoring at least one of (i) an X-ray tube anode operating condition, (ii) an X-ray tube cathode operating condition, (iii) an X-ray tube operating voltage, and (iv) a mode in which the scanner was operating when the malfunction was detected.

11. A medical diagnostic scanner which cycles through a sequence of operating modes comprising:

means for non-invasively examining a portion of a patient disposed in an examination region;

a detection means for producing electronic detector data indicative of the non-invasive examination;

an image reconstruction for reconstructing an image representation from the electronic data;

a monitor means for continuously monitoring which of the operating modes the scanner is in;

a latch means operatively connected with the monitor means for selectively latching the monitored operating mode;

a fault detection means for detecting a scanner malfunction, the fault detection means being operatively connected with the latch means for causing the latch means to latch the monitored operating mode before the detected malfunction cascades and affects other monitored conditions in response to a detected malfunction such that a snap shot of the operating mode when the malfunction occurred is latched; and, a display means for displaying an indication of the latched operating mode, such that the operating mode when the malfunction occurred is retrievable to assist in diagnosing a cause of the malfunction.

12. A method of monitoring a medical electronic apparatus for malfunctions, the method comprising:
   (a) continuously, transiently monitoring a plurality of ambient operating conditions of the medical electronic apparatus;
   (b) in response to a detected malfunction, instantaneously freezing each of the ambient monitored conditions in temporary storage;
   (c) transferring the frozen monitored conditions from temporary storage into a memory to create a malfunction history, such that the frozen monitored conditions provide a snap shot of the monitored conditions at each failure.

13. The method as set forth in claim 12 wherein the medical electronic apparatus cycles through a plurality of operating modes and wherein the monitoring step includes monitoring the operating mode such that the operating mode when the malfunction is detected is latched and transfered to the memory as part of the malfunction history.

14. The method as set forth in claim 12 wherein the monitoring step includes monitoring an apparatus operating mode.

15. The method as set forth in claim 12 wherein the monitoring step includes monitoring x-ray tube operating parameters.

16. The method as set forth in claim 12 further including:
   repeating steps (a), (b), and (c) for each of a plurality of medical electronic apparatae;
   at selected intervals, polling the memory of each apparatus from a central location to retrieve the malfunction history; and,
   storing and updating the retrieved malfunction history of each apparatus at the central location wherein the monitoring step includes monitoring a CT scanner x-ray tube operating parameters.

17. The method as set forth in claim 16 further including at the central location analyzing the retrieved malfunction histories and scheduling repair and maintenance in accordance therewith.

18. A method of monitoring a CT scanner for malfunctions, which CT scanner includes an x-ray tube mounted for rotation about a scan circle, the x-ray tube including an evacuated envelope, a rotatable anode disposed in the envelope, means for rotating the anode, and at least one cathode disposed in the envelope, an anode rotating means power supply for supplying motive power to the anode rotating means, a cathode power supply for providing a heating current to the cathode, a tube power supply for providing an electrical potential between the anode and the cathode, an x-ray detector array disposed across the scan circle from the x-ray tube to receive x-rays which have traversed a region of interest of a patient, rotating means for rotating the x-rays around the scan circle, an image reconstruction means for reconstructing image representations, the image reconstruction means including means for receiving information from the detector array about intensities of the x-rays which have traversed the region of interest and reconstructing an image of a cross section of the patient, the method comprising:

monitoring the anode to determine whether the anode is rotating;

monitoring the cathode to determine whether a selected heating current is provided thereto;

monitoring the electrical potential between the anode and the cathode to determine whether a selected electrical potential is applied therebetween;

causing an indication of the monitored anode rotation, the monitored cathode current, and the monitored tube power electrical potential to be stored temporarily in response to detecting a malfunction and before the detected malfunction cascades and changes the monitored anode rotation cathode current, and electrical potential indication; and, transferring the temporarily stored indication of monitored anode rotation, cathode current, and the tube electrical potential to long term memory after each of a plurality of malfunctions to create a malfunction history.

19. The method as set forth in claim 18 further including transferring the stored malfunction histories to a central location at selected intervals.

20. The method as set forth in claim 18 wherein the CT scanner cycles through a plurality of operating modes and further including monitoring the scanner operating mode, storing the monitored mode in response to the detected malfunction, and recording the monitored mode.

21. The method as set forth in claim 18 further including in response to the detected malfunction, causing the scanner to shift into a phase down mode in which the potential between the anode and cathode is removed and the cathode is cooled at a controlled rate.

* * * * *